United States Patent [19]

Colgrove et al.

[11] 4,454,359
[45] Jun. 12, 1984

[54] PROCESS FOR DRYING ALCOHOLS

[75] Inventors: Donald A. Colgrove; Howard L. Schoggen; Kenneth D. Wray, all of Memphis, Tenn.

[73] Assignee: The Procter & Gamble Company, Cincinnati, Ohio

[21] Appl. No.: 390,620

[22] Filed: Jun. 21, 1982

[51] Int. Cl.³ .................... C07C 29/86; C07C 31/10
[52] U.S. Cl. ................................ 568/916; 536/101; 568/918; 568/919
[58] Field of Search ...................... 568/916, 918, 919

[56] References Cited

U.S. PATENT DOCUMENTS

| | | | |
|---|---|---|---|
| 1,350,254 | 8/1920 | Frankforter | 568/916 |
| 1,452,206 | 4/1923 | Mann, Jr. | 568/916 |
| 2,022,274 | 11/1935 | Brooks | 260/106 |
| 2,461,048 | 2/1949 | Frejacques | 202/57 |
| 2,517,577 | 8/1950 | Klug et al. | 260/231 |
| 2,534,259 | 12/1950 | Gee et al. | 260/643 |
| 2,668,863 | 2/1954 | Norris | 260/643 |
| 2,680,737 | 6/1954 | Grassie et al. | 260/233 |
| 2,680,738 | 6/1954 | Laughlin | 260/233 |
| 2,696,493 | 12/1954 | Rottig | 260/450 |
| 2,696,508 | 12/1954 | Wilson | 260/643 |
| 3,105,099 | 9/1963 | Duerden | 260/643 |
| 3,589,364 | 6/1971 | Dean et al. | 128/284 |
| 3,678,031 | 7/1972 | Schoggen | 260/231 CM |
| 3,898,291 | 8/1975 | Darsi et al. | 260/643 |
| 3,990,952 | 11/1976 | Katzen et al. | 203/33 |

FOREIGN PATENT DOCUMENTS

| | | | |
|---|---|---|---|
| 1505547 | 11/1967 | France | 568/918 |
| 310623 | 5/1929 | United Kingdom | 568/918 |
| 877622 | 9/1961 | United Kingdom | 568/916 |

OTHER PUBLICATIONS

Ginnings, P. M. and Z. T. Chen, "Ternary Systems: Water, Isopropanol and Salts at 25°," *Journal of American Chemical Society*, vol. 53, pp. 3765-3769, (1931).
Steven, H. (ed), *Solubilities of Inorganic and Organic Compounds*, vol. 2, part 1, pp. 106, 128, and 146.

*Primary Examiner*—J. E. Evans
*Attorney, Agent, or Firm*—Milton B. Graff, IV; John V. Gorman; Richard C. Witte

[57] ABSTRACT

A process for the recovery of a water soluble alcohol from an aqueous mixture of the alcohol comprises incorporating in the mixture at least about 0.5% of a base selected from the group consisting of ammonium or alkali or alkaline metal hydroxide, ammonium or an alkali or alkaline metal carbonate or mixtures thereof; and at least about 0.2% of an electrolyte. The aqueous-alcohol mixture separates into two immiscible layers, and the layers are separated.

10 Claims, 1 Drawing Figure

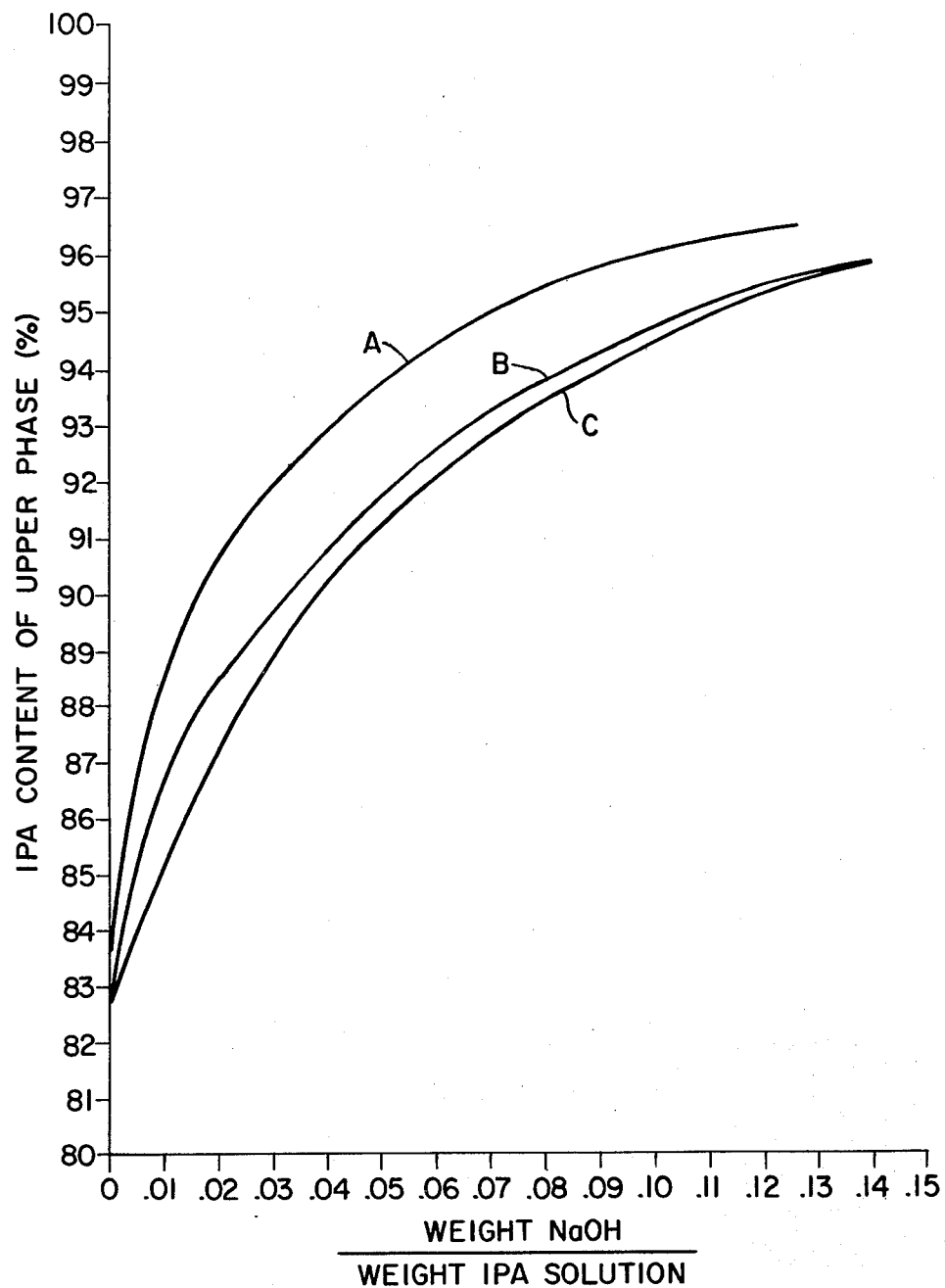

PROCESS FOR DRYING ALCOHOLS

TECHNICAL FIELD

This invention relates to the dehydration of aqueous-alcohol mixtures and, more specifically, to the dehydration of aqueous-alcohol mixtures by the addition of a base and an electrolyte which causes a separation of the mixture into two immiscible liquid layers, the upper layer being alcohol-rich.

BACKGROUND OF THE INVENTION

Water soluble alchols having more than one carbon atom are utilized in many industrial processes where they often become combined with water thus forming aqueous-alcohol mixtures. For most such industrial processes, it is necessary to recover the alcohol if utilization of the process is to be economically feasible. Processes for the manufacture of carboxymethyl cellulose (CMC) and other cellulose derivatives often utilize water soluble alcohols; such processes will be used herein to illustrate the process of the present invention; however, the present invention is not limited to such processes.

The most common process used to recover water soluble alcohols from aqueous-alcohol mixtures is distillation. Many of the water soluble alcohols form azeotropic mixtures with water and cannot be completely dehydrated by simple binary distillation techniques. Even where substantial dehydration of alcohol-water mixtures can be achieved by distillation, distillation has a disadvantage of requiring high energy input in order to achieve the separation. Also, a distillation process requires substantial startup and shutdown times to bring the system to equilibrium conditions so that the desired separation of components is achieved. The loss of 1-2% or more of the alcohol being recovered by distillation is common.

It is known that dehydration of certain water soluble alcohols can be achieved by the addition of a base or an electrolyte to an aqueous-alcohol mixture to cause separation of the mixture into two immiscible layers, the upper layer of which is alcohol-rich. U.S. Pat. No. 1,452,206 issued to Mann on Apr. 17, 1923, discloses the dehydration of higher alcohols, that is, of alcohols containing three or more carbon atoms, especially isopropyl alcohol (IPA), by the addition of caustic alkali such as sodium hydroxide or potassium hydroxide to cause the formation of two immiscible layers, the upper layer being alcohol-rich. Similar dehydration processes are disclosed in U.S. Pat. No. 2,461,048 issued to Frejacques on Feb. 8, 1949, for normal propyl alcohol and isopropyl by the addition of ammonium carbonate; and by U.S. Pat. No. 2,534,259 issued to Gee & Bossche on Dec. 19, 1950, for ethanol by the addition of aluminum sulfate. However, such processes have not been used in industrial applications due to the cost of the chemicals required, or the impurities introduced into the recovered alcohol.

Information concerning the equilibrium of IPA-water-salt mixtures for many different salts is presented in Ginnings, P. M., and Z. T. Chen, "Ternary Systems: Water, Isopropanol and Salts at 25°," *Journal of American Chemical Society*, Vol. 53, pages 3765–9 (1931); and Steven, H. (ed.), *Solubilities of Inorganic and Organic Compounds*, Vol. 2, Part 1, pages 105, 128, and 146.

SUMMARY OF THE INVENTION

It is an object of the present invention to achieve recovery of a water soluble alcohol from an aqueous-alcohol mixture by dehydration of the aqueous-alcohol mixture.

It is a further object of the present invention to achieve recovery of a water soluble alcohol from an aqueous-alcohol mixture using minimum energy input.

It is a still further object of the present invention to achieve recovery of a water soluble alcohol from an aqueous-alcohol mixture with minimal loss of the alcohol.

It is also an object of the present invention to achieve recovery of a water soluble alcohol from an aqueous-alcohol mixture by a process which requires minimal startup and shutdown times.

It is a further object of the present invention to achieve recovery of a water soluble alcohol from an aqueous-alcohol mixture such that the recovered alcohol is drier than an azeotropic mixture of the alcohol and water.

It is also an object of the present invention to achieve recovery of a water soluble alcohol from an aqueous-alcohol mixture by incorporating therein chemical constituents which will cause the mixture to separate into an alcohol-rich layer and a water/chemical constituent-rich layer.

It is a further object of this invention to achieve recovery of a water soluble alcohol from an aqueous-alcohol mixture by incorporating therein a minimum quantity of chemical constituents.

These and other objects will become apparent from the detailed description which follows.

The invention described herein is a process for the recovery of a water soluble alcohol having more than one carbon atom from an aqueous mixture of that alcohol. At least about 0.5% of a base selected from the group consisting of ammonium or an alkali or alkaline metal hydroxide, ammonium or an alkali or alkaline metal carbonate, or mixtures thereof, and at least about 0.2% of an electrolyte are incorporated into the aqueous-alcohol mixture wherein the mixture separates into two immiscible layers. The layers are separated.

BRIEF DESCRIPTION OF THE DRAWINGS

The FIGURE is a graph showing the dehydration of isopropyl alcohol achieved by the process of the present invention.

DETAILED DESCRIPTION OF THE INVENTION

The present invention involves the dehydration of water soluble alcohols. As used herein, the term "water soluble alcohols" refers to alcohols having more than one carbon atom that are totally miscible with water, or are partially miscible with water to an extent of at least 5% at 20° C. The water soluble alcohols preferred for use with the present invention are totally miscible with water, such as ethanol; more preferred are those alcohols that are totally miscible with water and have more than two carbon atoms, such as isopropyl alcohol, and tertiary butyl alcohol. The process of the present invention is particularly useful for the dehydration of isopropyl alcohol (IPA). The process for dehydration of water soluble alcohols of the present invention is achieved by incorporating a base and an electrolyte in an aqueous mixture of the alcohol.

All percentages expressed herein are weight/weight percentages unless otherwise specified.

The Base

The base is selected from the group consisting of ammonium or an alkali or alkaline metal hydroxide, ammonium or an alkali or alkaline metal carbonate, or mixtures thereof. With regard to the dehydration of IPA-water mixtures, the preferred base is sodium hydroxide, potassium hydroxide, sodium carbonate or mixtures thereof; especially preferred is sodium hydroxide.

The quantity of base incorporated in the aqueous-alcohol mixture to achieve dehydration according to the present invention is a concentration of preferably greater than about 0.5% in the aqueous-alcohol mixture. A more preferred range of base concentration in the mixture if from about 1% to about 12%; especially preferred is from about 2% to about 8%.

The Electrolyte

The electrolyte consists of at least one ionic substance. With regard to the separation of aqueous-IPA mixtures, the preferred electrolyte is sodium chloride, potassium chloride, sodium sulfate, sodium nitrate, sodium glycolate, or sodium monochloroacetate, mixtures thereof, or mixtures thereof with other ionic substances; more preferred are sodium chloride, glycolic acid, sodium glycolate, or sodium monochloroacetate, mixtures thereof, or mixtures thereof with other ionic substances; especially preferred are mixtures consisting essentially of sodium chloride, glycolic acid and/or sodium glycolate, and sodium monochloroacetate.

The quantity of electrolyte incorporated in the aqueous-alcohol mixture to achieve dehydration according to the present invention is preferably a concentration greater than about 0.2% in the aqueous-alcohol mixture. An especially preferred concentration of electrolyte in the mixture is greater than 0.5%. The electrolyte or some of its components are typically at their saturation level in the aqueous-alcohol mixture.

The concentrations of base and electrolyte incorporated in the aqueous-alcohol mixture must be sufficient to cause the mixture to separate into two immiscible layers. The base alone is generally more effective than the electolyte alone in causing separation of the alcohol and water into separate layers. However, incorporation of the electrolyte in the system substantially enhances the separation that would be achieved by using the base alone. The upper layer thus formed is alcohol-rich compared to the starting aqueous-alcohol mixture. The immiscible liquid layers are separated.

The dehydration of IPA according to the present invention is of particular interest with regard to the recovery of IPA for reuse in the manufacture of cellulose derivatives, especially carboxymethyl cellulose (CMC) and modified CMC's.

The manufacture of CMC and other cellulose derivatives generally begins with the preparation of alkali cellulose by a process such as that disclosed in U.S. Pat. Nos. 2,680,737 issued to Grassie & Wallis, and 2,680,738 issued to Laughlin, both on June 8, 1954, both of which are incorporated herein by reference. An aqueous-alcohol (preferably aqueous-IPA) slurry of alkali cellulose is reacted with monochloroacetic acid dissolved in alcohol to produce CMC and other cellulose derivatives.

The resulting cellulose derivative solids are separated from the liquid phase, for example, by filtration. The remaining liquid phase is an aqueous-IPA mixture containing certain byproduct electrolytes, mainly sodium chloride, glycolic acid, sodium glycolate, and sodium monochloroacetate. The glycolic acid and sodium glycolate are produced by the hydrolysis of monochloroacetic acid and sodium monochloroacetate during the production of the cellulose derivatives. Such processes are disclosed for the manufacture of CMC and other cellulose derivatives in U.S. Pat. Nos. 2,517,577 (CMC) issued to Klug & Tinsley on Aug. 8, 1950; 3,589,364 (bibulous cellulosic fibers) issued to Dean & Ferguson on June 29, 1971; and 3,678,031 (essentially acidic cellulosic fibers) issued to Schoggen on July 8, 1972; all of which are incorporated herein by reference. These references all disclose processes in which the product fibers are removed from an aqueous-alcohol phase, especially aqueous-IPA mixtures containing byproduct electrolytes.

The aqueous/alcohol phase remaining after removal of the product fibers in such processes is hereinafter referred to as "used diluent." A typical composition of used diluent is about 80–92% IPA, about 8–18% water, and about 0.5–2% dissolved byproduct electrolytes. Typically the dissolved electrolytes are a mixture comprising about 25–50% sodium chloride, 0–25% glycolic acid and/or sodium glycolate, and 25–75% sodium monochloroacetate.

In order to achieve an economic process, it is necessary to recover the alcohol from the used diluent. In recovering IPA from the used diluent according to the present invention, the electrolyte is present in the used diluent as the byproduct electrolytes described hereinabove and need not be added separately. A suitable quantity of base as described hereinabove is incorporated in the used diluent to cause separation of the used diluent into two immiscible layers. The layers are separated.

Over 99.5% of the IPA in the used diluent is typically recovered in the upper layer. The recovered IPA typically contains from about 3% to about 14% water and from about 0.25% to about 1% nonvolatile material (primarily base and electrolyte).

TEST PROCEDURES AND EXAMPLES

The following Examples are presented as illustrations of the present invention; they are not intended to limit the scope of the invention in any way.

Used diluent may be acidic, neutral or alkaline; alcohol recovered by the process of the present invention is alkaline. In analyzing the acidity or alkalinity of used diluent and recovered alcohol by the method described hereinbelow, it is assumed that all acidity is due to glycolic acid and that all alkalinity is due to sodium hydroxide in the solutions. The inorganic chloride content of the solutions is determined by silver nitrate titration and is reported as percent sodium chloride. Organic chloride content of the solutions is determined by converting it to inorganic chloride and titrating it with silver nitrate; the organic chloride is reported as percent sodium monochloroacetate. Total neutralized solids of the solutions is determined. The equivalent amounts of sodium chloride, sodium monochloroacetate, and either glycolic acid (neutralized to sodium glycolate for originally acidic solutions) or sodium hydroxide (neutralized to sodium sulfate for originally alkaline solutions) are subtracted from the total solids found and any remainder solids are assumed to be sodium glycolate. The water and alcohol fractions of the solutions are determined by gas chromatography analysis.

The following test procedures were used to analyze used diluent and recovered IPA solutions in the Examples:

Acid or Base Determination

Twenty to twenty-five grams of the used diluent or recovered alcohol, accurately weighed, is transferred to a beaker containing about 50 milliliters of water, Phenolphthalein is added and, depending on whether the solution is acidic or basic, it is titrated with standard 0.1 N sodium hydroxide or standard 0.1 N sulfuric acid. The percent glycolic acid or the percent sodium hydroxide is then calculated as shown in the equations below:

$$\% \text{ glycolic acid} = \frac{ml_{NaOH} \times N_{NaOH} \times 7.6}{\text{Wt. Sample}}$$

$$\% \text{ NaOH} = \frac{ml_{H2SO4} \times N_{H2SO4} \times 4.0}{\text{Wt. Sample}}$$

Sodium Chloride

The neutral solution from the acid or base determination is diluted with water to 250 ml. A suitable aliquot is titrated with standard 0.05 N silver nitrate solution to a potassium chromate end point. The sodium chloride content is calculated as follows:

$$\% \text{ NaCl} = \frac{ml_{AgNO3} \times N_{AgNO3} \times 5.84}{\text{Wt. Sample}}$$

Sodium Monochloroacetate

Sodium monochloroacetate (NaMCA) is analyzed by hydrolyzing organic chlorine to chloride ion and calculating the increase in chloride obtained over that determined under the sodium chloride determination.

A sample of the used diluent or recovered alcohol weighing between 20 and 25 grams is accurately weighed into a 250-ml beaker and diluted with 50 ml of water. To the solution in the beaker is added 25 ml of 1 N sodium hydroxide solution, and the contents are covered with a watch glass and digested in a boiling water bath for two and one-half hours. The pH in the solution is adjusted to between 6 and 10 with 12 N sulfuric acid, diluted to 250 ml in a volumetric flask, and the chloride content is determined by the method indicated above on an aliquot. The NaMCA content is calculated as follows:

$$\% \text{ NaMCA} = \frac{\left[(ml_{AgNO3} \times N_{AgNO3}) - \frac{\% \text{ NaCl} \times \text{Wt. Sample}}{5.84}\right] \times 11.65}{\text{Wt. Sample}}$$

Total Neutralized Solids

About 25 ml of the used diluent or recovered alcohol is transferred into the tared weighing bottle which is covered and accurately weighed. Using the acid or base content calculated above, the amount of either 0.1 N sulfuric acid or 0.1 N sodium hydroxide needed to neutralize the liquor is added. The sample is evaporated to dryness using a hot water bath until all of the alcohol is gone. The weighing bottle is then transferred to an oven and the residue is dried at 105° C. to constant weight. The percent solids in the liquor is calculated as follows:

$$\% \text{ Total Solids} = \frac{\text{Dry Wt.} \times 100}{\text{Wet Wt.}}$$

Sodium Glycolate

The sodium glycolate content of the used diluent or recovered alcohol is calculated by subtracting the sodium chloride, sodium monochloroacetate, and sodium sulfate equivalent to the sodium hydroxide content (or sodium glycolate equivalent to the glycolic acid content) from the total solids.

% Sodium glycolate = T-(C+M+1.29G+1.78H)
Where
  T = % Total Solids
  C = %NaCl
  M = % Sodium monochloroacetate
  G = % Glycolic acid (for acidic liquors)
  H = % NaOH (for basic liquors)

% Water and IPA by Gas Chromatography

The IPA and water content of solutions is determined by gas chromatography using a standard gas chromatograph with a thermal conductivity detector set up as follows:
  Column—6 ft. × ⅛" as packed with Poropak Q 100/120
  Carrier—Helium, flow 30 ml/min
  Injection Port—125° C., Detector 275° C., Detector Current 150 ma
  Column Oven = Temperature programmed from 70° C. to 250° C. at 15° C./min
  Integrator to give "counts" representing area of peaks The system was calibrated using standard water/IPA solutions calculated as % by weight to determine detector response factors for water and IPA.

The samples were chromatographed using a 5 μl sample size and the water and IPA contents calculated from the peak area counts and the previously determined response factors as follows:
  Area Counts (H2O) × response factor (H2O) = A
  Area Counts (IPA) × response factor (IPA) = B $$\% \text{ H}_2\text{O} = \frac{A}{A+B} \times 100$$

$$\% \text{ IPA} = \frac{B}{A+B} \times 100$$

% water and % IPA thus obtained are based on the volatile fraction of the solutions and do not reflect any solids content of the solutions.

EXAMPLE 1

A quantity of used diluent comprising 83.7% IPA, 0.47% sodium chloride, 0.19% glycolic acid, and 0.33% sodium monochloroacetate was divided into measured volume samples. The used diluent containing the electrolytes was a single, homogeneous phase. To the samples various amounts of 50% aqueous solution sodium hydroxide were added such that the weight of sodium hydroxide added to the used diluent was between 0.005 gram NaOH and 0.13 gram NaOH per gram used diluent. In each case, the addition of sodium hydroxide caused a separation of the used diluent into two immiscible layers. The top layer of each sample was analyzed for its IPA content. The results are presented in Table 1 below and are shown as Curve A in the FIGURE.

TABLE 1

| Weight of NaOH added/Weight of Used Diluent | IPA Content of Upper Phase (%) |
|---|---|
| 0.007 | 88.0 |
| 0.011 | 89.5 |
| 0.041 | 92.4 |
| 0.068 | 95.8 |
| 0.097 | 95.8 |
| 0.126 | 96.6 |

EXAMPLE 2

A distilled water-IPA solution comprising 82.7% IPA was saturated with 0.61% sodium chloride. The resulting mixture was divided into measured volume samples to which various amounts of 50% aqueous solution of sodium hydroxide were added such that the weight of sodium hydroxide incorporated into the mixture was added 0.01 gram NaOH and 0.14 gram NaOH per gram of the starting IPA-water-NaCl solution. In each case, the addition of sodium hydroxide caused a separation of the mixture into two immiscible layers. The top layer of each sample was analyzed for its IPA content. The results are presented in Table 2 below and are shown as Curve B in the FIGURE.

TABLE 2

| Weight of NaOH added/Weight of IPA-Water-NaCl Solution | IPA Content of Upper Phase (%) |
|---|---|
| 0.010 | 86.9 |
| 0.020 | 88.4 |
| 0.030 | 89.8 |
| 0.040 | 90.4 |
| 0.060 | 92.6 |
| 0.080 | 93.8 |
| 0.100 | 94.7 |
| 0.120 | 95.4 |
| 0.140 | 95.9 |

EXAMPLE 3

A distilled water-IPA solution comprising 82.7% IPA was divided into measured volume samples. To the samples various amounts of 50% aqueous solution of sodium hydroxide were added such that the weight of sodium hydroxide incorporated into the mixture was between 0.01 gram NaOH and 0.14 gram NaOH per gram of the starting IPA-water solution. In each case, the addition of sodium hydroxide caused a separation of the mixture into two immiscible layers. The top layer of each sample was analyzed for its IPA content. The results are presented in Table 3 below and are shown as Curve C in the FIGURE.

TABLE 3

| Weight of NaOH added/Weight of IPA-Water Solution | IPA Content of Upper Phase (%) |
|---|---|
| 0.005 | 84.0 |
| 0.010 | 85.0 |
| 0.010 | 85.1 |
| 0.020 | 87.2 |

TABLE 3-continued

| Weight of NaOH added/Weight of IPA-Water Solution | IPA Content of Upper Phase (%) |
|---|---|
| 0.021 | 87.2 |
| 0.030 | 88.9 |
| 0.040 | 90.3 |
| 0.042 | 90.4 |
| 0.060 | 92.3 |
| 0.068 | 92.6 |
| 0.080 | 93.7 |
| 0.095 | 94.4 |
| 0.100 | 94.2 |
| 0.120 | 95.3 |
| 0.124 | 95.5 |
| 0.140 | 96.0 |

Comparison of the data in Tables 1, 2 and 3 and Curves A, B and C of the FIGURE shows the surprising enhancement of dehydration of IPA by separation of an immiscible aqueous layer achieved when both a base and an electrolyte are present in the system.

EXAMPLE 4

A series of batches of essentially acidic sodium carboxymethyl cellulose were manufactured by a process similar to that described in Example 1 of U.S. Pat. No. 3,678,031. Twenty-two pounds of sheeted cellulose were disintegrated in aqueous-IPA with vigorous agitation. 36.2 pounds of a 50% sodium hydroxide aqueous solution was added. The amount of IPA and water was adjusted so that the total diluent to cellulose ratio, including the water accompanying the sodium hydroxide, was 30 to 1, while the water to cellulose ratio was 5.50 to 1; consequently, the IPA to water ratio was 4.45 to 1. Included in the above amounts is about 1 part of water per part of cellulose that was used to improve disintegration of the fibers in the diluent by direct addition to the dry cellulose. After contacting the slurried cellulose with sodium hydroxide for 30 minutes at ambient temperatures, 26.05 pounds of monochloroacetic acid was added while agitation was continued. The temperature of the reaction vessel was increased to 100° C. and the reaction was allowed to proceed for 2 hours. At the end of the specified reaction period, the cellulose derivative solids were separated from the aqueous-IPA used diluent by filtration.

IPA was recovered from the used diluent by the process of the present invention and the recovered IPA was used in the production of the next batch of the series using the above process. (Pure IPA and water were used for the first batch.) A small amount of makeup IPA and water were used in the subsequent batches. The water and electrolyte composition of the used diluent obtained from each of five consecutive batches is shown in Table 4.

TABLE 4

| | | Electrolyte Content (%) | | | |
|---|---|---|---|---|---|
| Batch No. | Water Content* (%) | Sodium Chloride | Glycolic Acid | Sodium Glycolate | Sodium Monochloroacetate |
| 1 | 16.3 | 0.66 | 0.31 | 0.18 | 0.57 |
| 2 | 16.3 | 0.73 | 0.31 | 0.19 | 0.69 |
| 3 | 16.3 | 0.64 | 0.35 | 0.10 | 0.61 |
| 4 | 16.3 | 0.59 | 0.32 | 0.15 | 0.51 |
| 5 | 16.3 | 0.63 | 0.34 | 0.13 | 0.65 |

*Water content was calculated based on the water in recycled solvent, water added, and water formed by reaction during the batch.

To recover the IPA from the used diluent from each batch, the used diluent was pumped into an agitated vessel. A quantity of sodium hydroxide (50% aqueous solution) was added to the used diluent such that the ratio of NaOH (100%) to used diluent was 0.0234. The sodium hydroxide solution and used diluent were thoroughly mixed and were then allowed to stand for about 15 minutes to separate into two phases. The heavier phase primarily consisting of water, electrolytes and sodium hydroxide was discarded. A sample of the lighter (upper) phase was analyzed and found to have the compositions shown in Table 5.

TABLE 5

| Batch No. | Water Content (%) | NaOH Content (%) | Electrolyte Content (%) | | |
|---|---|---|---|---|---|
| | | | Sodium Chloride | Sodium Glycolate | Sodium Monochloroacetate |
| 1 | 11.5 | 0.09 | 0.11 | 0.14 | 0.01 |
| 2 | 11.9 | 0.09 | 0.13 | 0.16 | 0.01 |
| 3 | 11.5 | 0.08 | 0.09 | 0.13 | 0.17 |
| 4 | 11.1 | 0.13 | 0.07 | 0.17 | 0.24 |
| 5 | 11.1 | 0.08 | 0.09 | 0.13 | 0.17 |

EXAMPLE 5

A series of batches to produce sodium carboxymethyl cellulose were manufactured by a process similar to that described in Example 3 of U.S. Pat. No. 2,517,577. Fifteen pounds of a sheeted cellulose were disintegrated in aqueous-IPA with vigorous agitation. 16.6 pounds of a 50% sodium hydroxide aqueous solution was added. The amount of IPA and water was adjusted so that the total diluent to cellulose ratio, including the water accompanying the sodium hydroxide, was 22 to 1 while the water to cellulose ratio was 1.87 to 1; consequently, the IPA to water ratio was 10.76 to 1. Included in the above amount is 0.3 pounds of water in which was already present in the sheeted cellulose charge prior to grinding and dispersing it in the diluent. After contacting the slurried cellulose with sodium hydroxide for 30 minutes at ambient temperatures, 10.9 pounds of monochloroacetic acid was added while agitation was continued. The temperature of the reaction vessel was increased to 75° C. and the reaction was allowed to proceed for 40 minutes. At the end of the specified reaction period, the CMC solids were separated from the aqueous-IPA used diluent by filtration.

The IPA was recovered from the used diluent by the process of the present invention and the recovered IPA was used in the next batch of the series using the above process. (Pure IPA and water were used for the first batch.) The used diluent from batches 1–4 had water and electrolyte content as shown in Table 6.

TABLE 6

| Batch No. | Water Content (%) | Electrolyte Content (%) | | | | NaOH Added (Wt. NaOH/ Wt. Used Diluent) |
|---|---|---|---|---|---|---|
| | | Sodium Chloride | Glycolic Acid | Sodium Glycolate | Sodium Monochloroacetate | |
| 1 | 11.1 | 0.13 | 0 | 0 | 0.54 | 0.0465 |
| 2 | 7.9 | 0.11 | 0 | 0.01 | 0.35 | 0.0558 |
| 3 | 9.9 | 0.16 | 0 | 0.12 | 0.26 | 0.0412 |
| 4 | 9.5 | 0.15 | 0 | 0.03 | 0.37 | 0.0480 |

After each batch, IPA was recovered from the used diluent according to the process described in Example 4. The quantity of sodium hydroxide added to the used diluent varied for each batch and is shown in Table 6. The recovered IPA contained water, sodium hydroxide, and electrolytes as shown in Table 7.

TABLE 7

| Batch No. | Water Content (%) | NaOH Content (%) | Electrolyte Content (%) | | |
|---|---|---|---|---|---|
| | | | Sodium Chloride | Sodium Glycolate | Sodium Monochloroacetate |
| 1 | 4.1 | 0.14 | 0.02 | 0.04 | 0.15 |
| 2 | 3.3 | 0.18 | 0.01 | 0.04 | 0.10 |
| 3 | 4.8 | 0.16 | 0.01 | 0.09 | 0.13 |
| 4 | 4.1 | 0.14 | 0.01 | 0.04 | 0.07 |

After recovering the IPA from each batch, a small amount of IPA and water was added to make up for losses and the recovered IPA was used to produce the subsequent batch.

Sodium hydroxide may be recovered from the heavier (lower) phase before discarding it, and can be reprocessed and recycled in the CMC manufacturing process.

While particular embodiments of the present invention have been illustrated and described, it would be obvious to those skilled in the art that various changes and modifications can be made without departing from the spirit and scope of the invention. It is intended to cover, in the appended claims, all such modifications that are within the scope of the invention.

What is claimed is:

1. A process for the recovery of isopropyl alcohol from an aqueous mixture of said isopropyl alcohol comprising incorporating in said mixture
   (a) a base selected from the group consisting of ammonium or an alkali or alkaline metal hydroxide, ammonium or an alkali or alkaline metal carbonate, or mixtures thereof, at a concentration of greater than about 0.5% in said mixture; and
   (b) an electrolyte comprising sodium chloride, glycolic acid, sodium glycolate, or sodium monochloroacetate, or mixtures thereof, at a concentration of from about 0.2% to about 2% in said mixture;

whereby said mixture separates into two immiscible layers; and separating said layers.

2. The process of claim 1 wherein said base is at a concentration of from about 2% to about 8%.

3. The process of claim 2 wherein said electrolyte is at a concentration of from about 0.5% to about 2%.

4. The process of claim 3 wherein said base is sodium hydroxide.

5. The process of claim 4 wherein said electrolyte consists essentially of a mixture of sodium chloride, sodium glycolate and/or glycolic acid, and sodium monochloroacetate.

6. A process for the recovery of isopropyl alcohol from used diluent of a cellulose derivative manufacturing process, where said used diluent contains dissolved electrolyte at a concentration of from about 0.2% to about 2%, said electrolyte comprising sodium chloride, glycolic acid, sodium glycolate, or sodium monochloroacetate, or mixtures thereof, comprising the following steps:
   (a) separating said used diluent from a cellulose derivative;
   (b) adding to said used diluent a base selected from the group consisting of ammonium or an alkali or alkaline metal hydroxide, ammonium or an alkali or alkaline metal carbonate, or mixtures thereof, such that the resulting basic used diluent has a concentration of said base greater than about 0.5%;

(c) agitating said basic used diluent;

(d) allowing said basic used diluent to separate into two immiscible layers; and (e) separating said layers.

7. The process of claim 6 wherein said base concentration of said basic used diluent is from about 2% to about 8%.

8. The process of claim 7 wherein said electrolyte concentration of said used diluent is from about 0.5% to about 2%.

9. The process of claim 8 wherein said base is sodium hydroxide.

10. The process of claim 9 wherein said electrolyte consists essentially of a mixture of sodium chloride, sodium glycolate and/or glycolic acid, and sodium monochloroacetate.

* * * * *